(12) United States Patent
Koseoglu et al.

(10) Patent No.: US 11,267,769 B2
(45) Date of Patent: *Mar. 8, 2022

(54) CATALYTIC HYDRODEARYLATION OF HEAVY AROMATIC STREAMS CONTAINING DISSOLVED HYDROGEN WITH FRACTIONATION

(71) Applicant: Saudi Arabian Oil Company, Dhahran (SA)

(72) Inventors: Omer Refa Koseoglu, Dhahran (SA); Robert Peter Hodgkins, Dhahran (SA); Bruce Richard Beadle, Dhahran (SA); Vinod Ramaseshan, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 17/154,561

(22) Filed: Jan. 21, 2021

(65) Prior Publication Data

US 2021/0139393 A1 May 13, 2021

Related U.S. Application Data

(63) Continuation-in-part of application No. 16/594,768, filed on Oct. 7, 2019, now Pat. No. 10,899,685.

(51) Int. Cl.
*C07C 4/00* (2006.01)
*C07C 4/26* (2006.01)
(Continued)

(52) U.S. Cl.
CPC ............... *C07C 4/26* (2013.01); *B01D 3/143* (2013.01); *B01D 3/346* (2013.01); *B01J 8/0278* (2013.01);
(Continued)

(58) Field of Classification Search
CPC ............... B01D 3/143; B01D 3/346; B01J 2208/00849; B01J 8/0278; B01J 8/0492;
(Continued)

(56) References Cited

U.S. PATENT DOCUMENTS 3,053,760 A 9/1962 Henke et al.
3,067,128 A 12/1962 Kimberlin et al.
(Continued)

FOREIGN PATENT DOCUMENTS

GB 1155848 A 6/1969
WO 2005071045 A1 8/2005
(Continued)

OTHER PUBLICATIONS

International Search Report and Written Opinion of PCT Application No. PCT/US2020/054292 (SA51328) dated Feb. 4, 2021: pp. 1-13.

(Continued)

*Primary Examiner* — Sharon Pregler
(74) *Attorney, Agent, or Firm* — Bracewell LLP; Constance G. Rhebergen; Kevin R. Tamm

(57) ABSTRACT

Systems and methods for hydrodearylation of a hydrocarbon feed stream comprising non-condensed alkyl-bridged multi-aromatic hydrocarbons, the method including supplying a hydrogen feed to the hydrocarbon feed stream comprising non-condensed alkyl-bridged multi-aromatic hydrocarbons; mixing the hydrogen feed with the hydrocarbon feed stream to saturate the hydrocarbon feed stream with hydrogen gas to create a hydrogen-enriched liquid hydrocarbon stream; passing the hydrogen-enriched liquid hydrocarbon stream to a hydrodearylation reactor without a separate gaseous phase of hydrogen; allowing the hydrogen-enriched liquid hydrocarbon stream to react in presence of a catalyst under specific reaction conditions to produce a product stream (Continued)

comprising a reduced concentration of di-aromatic compounds and an increased concentration of mono-aromatic compounds compared to the hydrocarbon feed stream comprising non-condensed alkyl-bridged multi-aromatic hydrocarbons; and recovering, from the hydrodearylation reactor, a product stream for a downstream process, wherein the non-condensed alkyl-bridged multi-aromatic hydrocarbons include at least two benzene rings connected by an alkyl bridge group having at least two carbons, wherein the benzene rings are connected to different carbons of the alkyl bridge group.

48 Claims, 2 Drawing Sheets

(51) Int. Cl.
| | | |
|---|---|---|
| *C07C 7/09* | (2006.01) | |
| *B01J 8/02* | (2006.01) | |
| *B01D 3/14* | (2006.01) | |
| *B01D 3/34* | (2006.01) | |
| *B01J 8/04* | (2006.01) | |

(52) U.S. Cl.
CPC ............... *B01J 8/0492* (2013.01); *C07C 7/09* (2013.01); *B01J 2208/00849* (2013.01)

(58) Field of Classification Search
CPC ........... B01J 21/04; B01J 29/166; C07C 4/26; C07C 2521/04; C07C 2523/28; C07C 2523/38; C07C 2523/755; C07C 2529/08; C07C 7/09
See application file for complete search history.

(56) References Cited

U.S. PATENT DOCUMENTS

| | | | |
|---|---|---|---|
| 3,075,022 A | 1/1963 | Gammon et al. | |
| 3,116,345 A | 12/1963 | Slaymaker | |
| 3,204,007 A | 8/1965 | Taro et al. | |
| 3,291,850 A | 12/1966 | Carson | |
| 3,322,842 A | 5/1967 | Czajkowski et al. | |
| 3,349,145 A | 10/1967 | Uitti | |
| 3,445,379 A | 5/1969 | Hansen, Jr. | |
| 3,882,014 A | 5/1975 | Monday et al. | |
| 4,058,452 A | 11/1977 | Loboda | |
| 7,723,554 B2 | 5/2010 | Arca et al. | |
| 7,880,045 B2 | 1/2011 | Arca et al. | |
| 8,168,844 B2 | 4/2012 | Arca et al. | |
| 8,198,492 B2 | 6/2012 | Brady et al. | |
| 9,174,892 B2 | 11/2015 | Negiz et al. | |
| 10,053,401 B1 | 8/2018 | Beadle et al. | |
| 10,093,873 B2 | 10/2018 | Koseoglu et al. | |
| 10,294,172 B2 | 5/2019 | Beadle et al. | |
| 10,899,685 B1* | 1/2021 | Koseoglu | C07C 4/26 |
| 2016/0168488 A1 | 6/2016 | Eizenga et al. | |
| 2019/0241486 A1 | 8/2019 | Koseoglu et al. | |

FOREIGN PATENT DOCUMENTS

| | | |
|---|---|---|
| WO | 2005090525 A1 | 9/2005 |
| WO | 2008015027 A1 | 2/2008 |
| WO | 2009008879 A1 | 1/2009 |
| WO | 2018235113 A1 | 12/2018 |

OTHER PUBLICATIONS

Singh et al., "Kinetic and thermodynamic analysis of liquidphase benzene hydrogenation", American Institute of Chemical Engineers, vol. 45, Issue 5, May 1999, pp. 1059-1071.

U.S. Appl. No. 16/554,057, "Low-Sulfur Aromatic-Rich Fuel Oil Blending Component", filed Aug. 28, 2019, (SA51047).

U.S. Appl. No. 16/424,273, "Systems and Processes for Suppressing Heavy Polynuclear Aromatic Deposition in a Hydrocracking Process", filed May 28, 2019, (SA51046).

U.S. Appl. No. 16/592,591, "Two Stage Hydrodearylation Systems and Processes to Convert Heavy Aromatics Into Gasoline Blending Components and Chemical Grade Aromatics", filed Oct. 3, 2019, (SA51330).

* cited by examiner

CATALYTIC HYDRODEARYLATION OF HEAVY AROMATIC STREAMS CONTAINING DISSOLVED HYDROGEN WITH FRACTIONATION

PRIORITY

The present application is a continuation-in-part application of and claims priority to and the benefit of U.S. non-provisional patent application Ser. No. 16/594,768, filed Oct. 7, 2019, the entire disclosure of which is incorporated here by reference in its entirety.

BACKGROUND

Field

This disclosure relates to dearylation for streams containing heavy, non-condensed, multi-aromatic molecules during a hydrocarbon refining process. In particular, this disclosure relates to using a two-phase liquid-solid system with dissolved hydrogen to dearylate multi-aromatic molecules including two or more aromatic rings bridged by an alkyl group.

Description of Related Art

In an aromatics complex, a variety of process units are used to convert naphtha or pyrolysis gasoline into benzene, toluene and mixed xylenes, which are basic petrochemical intermediates used for the production of various other chemical products. In order to maximize the production of benzene, toluene, and mixed xylenes, the feed to an aromatics complex is generally limited from $C_6$ up to $C_{11}$ compounds. In most aromatics complexes, the mixed xylenes are processed within the complex to produce the particular isomer—para-xylene, which can be processed downstream to produce terephthalic acid.

This terephthalic acid is used to make polyesters, such as polyethylene terephthalate. In order to increase the production of benzene and para-xylene, the toluene and $C_9$ and $C_{10}$ aromatics are processed within the complex through a toluene, $C_9$, $C_{10}$ transalkylation/toluene disproportionation (TA/TDP) process unit to produce benzene and xylenes. Any remaining toluene, $C_9$, and $C_{10}$ aromatics are recycled to extinction. Compounds heavier than $C_{10}$ are generally not processed in the TA/TDP unit, as they tend to cause rapid deactivation of the catalysts used at the higher temperatures used in these units, often greater than 400° C.

When para-xylene is recovered from mixed xylenes by a selective adsorption process unit in the complex, the $C_8$ feed to the selective adsorption unit is processed to eliminate olefins and alkenyl aromatics such as styrene in the feed. Olefinic material can react and occlude the pores of the zeolite adsorbent. The olefinic material is removed by passing a $C_{8+}$ stream across a clay or acidic catalyst to react olefins and alkenyl aromatics with another (typically aromatic) molecule, forming heavier compounds ($C_{16+}$). These heavier compounds are typically removed from the mixed xylenes by fractionation. The heavy compounds cannot be processed in the TA/TDP unit due to their tendency to deactivate the catalyst and are generally removed from the complex as lower value fuels blend stock.

Also during hydrocarbon processing, compounds composed of an aromatic ring with one or more coupled alkyl groups containing three or more carbon molecules per alkyl group may be formed. Formation of these compounds may be from processes used by petroleum refiners and petrochemical producers to produce aromatic compounds from non-aromatic hydrocarbons, such as catalytic reforming. As many of these heavy alkyl aromatic compounds fractionate with the fractions containing greater than 10 carbon atoms, they are not typically sent as feedstock to the transalkylation unit, and instead are sent to gasoline blending or used as fuel oil.

High boiling point multi-aromatics are generally concentrated in the bottoms stream of a xylene rerun column in an aromatics recovery complex or "ARC." This bottoms stream is typically either further processed in a heavy aromatics column or used directly as a gasoline blending component. When sent to a heavy aromatics column, the nine-carbon and some of the ten-carbon molecules are fractionated overhead to be sent to a $C_7/C_9/C_{10}$ transalkylation unit for conversion to benzene and xylenes, while the heavy aromatics bottoms stream containing multi-aromatics is sent to be used as fuel oil, or sent for recovery of $C_{11}$ and $C_{12}$ molecules for use as solvents, or sent to a gasoline blending pool at the cost of quality, for example, undesirable color changes, density changes, and boiling point increases.

In a conventional three-phase hydrocarbon processing system, a liquid hydrocarbon phase and a gaseous hydrogen phase are passed to a fixed bed of solid catalyst particles. In the three-phase reactor, the hydrogen gas is transported from the gas phase to the liquid phase, across the gas/liquid interface. Hydrogen gas is then transported through the liquid to the external surface of the catalyst particles and then to the interior of the particle (for example, a zeolite particle). The hydrogen gas adsorbs at an active site on the catalyst surface. Liquid molecules are transported to the external surface of the catalyst, and then diffuse into the pores of the solid catalyst and adsorb on the surface. Both adsorbed molecules, hydrogen (gas) and hydrocarbon (liquid), react. The liquid products must diffuse from the interior of the catalyst to the external surface and then be transported from the external surface to the bulk liquid.

Conventional three-phase hydrocarbon processing systems are limited in their ability to carry out hydrodearylation for heavy hydrocarbon feeds.

SUMMARY

Applicant has recognized a need for systems and processes for the hydrodearylation of a stream containing non-condensed aromatic molecules that include two or more aromatic rings bridged by an alkyl group (for example, 1,1-diphenyl ethane or 1-phenyl-1-xylyl ethane). Such non-condensed aromatic molecules are formed, for example, in the de-olefinization step of an aromatic complex over acidic catalysts. By applying dissolved hydrogen in liquid fluid streams, systems and methods of the present disclosure hydrodearylate alky-bridged multi-aromatics to alkyl-aromatics in a two-phase reactor, and thus increase overall $C_6$-$C_8$ aromatics production and improve the blending suitability of rejected heavy aromatics compounds.

Embodiments disclosed here, for example FIG. 1, show two-phase systems for hydrodearylation of heavy aromatic streams. In some embodiments, liquid feedstock is fully saturated with hydrogen gas at or about the required temperature and pressure of a hydrodearylation reactor prior to the liquid phase contacting one or more solid catalyst for dearylation reactions in the hydrodearylation reactor. Embodiments disclosed here are operable in the absence of or without a separate hydrogen gas phase outside of hydrogen dissolved in a hydrocarbon liquid, for example saturating the hydrocarbon liquid. A hydrocarbon liquid fluid comprising heavy non-condensed, alkyl-bridged, multi-aromatic compounds and saturated with hydrogen can be fed into a reactor as a single phase (liquid) for reactions, making the system two phase, liquid (feed) and solid (catalyst). No hydrogen gas is required to be fed to the hydrodearylation reactor, and no separate hydrogen gas phase is required or produced in the hydrodearylation reactor.

In certain two-phase systems described here, hydrogen gas is transported to and dissolved in a liquid hydrocarbon phase in a mixer prior to entering a reactor with solid catalyst, and both hydrogen dissolved in a liquid hydrocarbon phase and the liquid hydrocarbon feedstock are sent to the reactor as one phase.

In certain embodiments, the hydrogen stream includes a recycled hydrogen stream and a makeup hydrogen stream. In certain embodiments, the hydrogen stream comprises at least 70% hydrogen by weight. The catalyst can be presented as one or more catalyst beds in the reactor. In certain embodiments, the catalyst bed is comprised of two or more catalyst beds.

The catalyst can include a support being at least one member of the group consisting of silica, alumina, and combinations thereof, and can further include an acidic component being at least one member of the group consisting of amorphous silica-alumina, zeolite, and combinations thereof. In certain embodiments, the catalyst includes an IUPAC Group 8-10 metal and an IUPAC Group 6 metal. In certain embodiments, the catalyst includes an IUPAC Group 8-10 metal being at least one member of the group consisting of iron, cobalt, and nickel, and combinations thereof and further includes an IUPAC Group 6 metal being at least one member of the group consisting of molybdenum and tungsten, and combinations thereof. In certain embodiments, the IUPAC Group 8-10 metal is 2 to 20 percent by weight of the catalyst and the IUPAC Group 6 metal is 1 to 25 percent by weight of the catalyst. In certain embodiments, the catalyst is comprised of nickel, molybdenum, ultrastable Y-type zeolite, and γ-alumina support.

In certain embodiments, the specific reaction conditions include an operating temperature of the reactor during the hydrodearylation reaction being in the range of about 200° C. to about 450° C. The operating temperature of the reactor during the hydrodearylation reaction can be about 300° C. The operating temperature of the reactor during the hydrodearylation reaction can be about 350° C.

Certain embodiments of the process further include the step of supplying, to the reactor, a recycled hydrocarbon stream containing unreacted alkyl-bridged non-condensed alkyl multi-aromatic compounds. The recycled hydrocarbon stream can be combined with the feed stream to form a combined feed stream being supplied to the reactor. The hydrogen stream can be combined with the combined feed stream to form a second combined stream being supplied to the reactor. Certain embodiments of the process further include the step of supplying the product stream to a separation zone to separate the product into a lighter hydrocarbon stream and a heavier hydrocarbon stream.

Therefore, disclosed here is a method for hydrodearylation of a hydrocarbon feed stream comprising non-condensed alkyl-bridged multi-aromatic hydrocarbons, the method including supplying a hydrogen feed stream to the hydrocarbon feed stream comprising non-condensed alkyl-bridged multi-aromatic hydrocarbons; mixing the hydrogen feed stream with the hydrocarbon feed stream to saturate the hydrocarbon feed stream with hydrogen gas to create a hydrogen-enriched liquid hydrocarbon stream; passing the hydrogen-enriched liquid hydrocarbon stream to a hydrodearylation reactor without a separate gaseous phase of hydrogen; allowing the hydrogen-enriched liquid hydrocarbon stream to react in the presence of a catalyst under specific reaction conditions as a liquid to produce a product stream comprising a reduced concentration of di-aromatic compounds and an increased concentration of mono-aromatic compounds compared to the hydrocarbon feed stream comprising non-condensed alkyl-bridged multi-aromatic hydrocarbons; and recovering, from the hydrodearylation reactor, a product stream for a downstream process, where the non-condensed alkyl-bridged multi-aromatic hydrocarbons include at least two benzene rings connected by an alkyl bridge group having at least two carbons, where the benzene rings are connected to different carbons of the alkyl bridge group.

In some embodiments of the method, the hydrocarbon feed stream comprises $C_{9+}$ compounds obtained from a xylene rerun column. In other embodiments of the method, the hydrocarbon feed stream comprises $C_{11+}$ compounds obtained from a xylene rerun column. Still in other embodiments, the hydrogen feed stream includes a recycled hydrogen stream and a makeup hydrogen stream. In yet other embodiments, the hydrogen feed stream comprises at least 70% hydrogen by weight. In certain embodiments, the catalyst is presented as a catalyst bed in the hydrodearylation reactor. Still in other embodiments, the catalyst bed includes two or more catalyst beds. In yet other embodiments, the catalyst includes a support being at least one member of the group consisting of silica, alumina, and combinations thereof, and further includes an acidic component being at least one member of the group consisting of amorphous silica-alumina, zeolite, and combinations thereof.

In some embodiments, the catalyst includes an IUPAC Group 8-10 metal being at least one member of the group consisting of iron, cobalt, and nickel, and combinations thereof and further includes an IUPAC Group 6 metal being at least one member of the group consisting of molybdenum and tungsten, and combinations thereof. Still in other embodiments, the IUPAC Group 8-10 metal is 2 to 20 percent by weight of the catalyst and the IUPAC Group 6 metal is 1 to 25 percent by weight of the catalyst. In some embodiments, the catalyst includes at least one of nickel, molybdenum, ultrastable Y-type zeolite, and γ-alumina support. In yet other embodiments, the catalyst includes a noble IUPAC Group 8-10 metal. Still in other embodiments, specific reaction conditions include an operating temperature of the hydrodearylation reactor being in the range of about 200° C. to about 450° C., with a pressure between about 5 barg and about 25 barg. In some embodiments, the operating temperature of the reactor is about 300° C. In other embodiments, the operating temperature of the reactor is about 350° C.

Still in other embodiments, the mixing step comprises a first mixing step and a second mixing step, where the first mixing step mixes a first hydrocarbon recycle stream with the hydrocarbon feed stream, and where the second mixing step mixes a second hydrocarbon recycle stream with the hydrocarbon feed stream. In some embodiments, the step of supplying a hydrogen feed stream comprises a first step of supplying a hydrogen feed stream and a second step of supplying a hydrogen feed stream, the first step of supplying a hydrogen feed stream occurring before the first mixing step, and the second step of supplying a hydrogen feed stream occurring before the second mixing step. Still in other embodiments, the first mixing step uses a static mixer to mix hydrogen, the hydrocarbon feed stream, and the first hydrocarbon recycle stream, and the second mixing step uses a static mixer to mix hydrogen, the hydrocarbon feed stream, and the second hydrocarbon recycle stream.

Certain embodiments of the method include the step of flowing the product stream to a separation zone with a hot separator to separate the product stream into a hydrodearylated gas tops stream and a hydrodearylated liquid bottoms stream, where a portion of the hydrodearylated liquid bottoms stream is recycled for mixing with the hydrogen feed stream and the hydrocarbon feed stream in the mixing step. Other embodiments of the method include the steps of flowing the hydrodearylated gas tops stream and a remaining portion of the hydrodearylated liquid bottoms stream to a stripper column of a fractionation zone, producing a light vapor stripper top stream and a heavy stripper column bottom stream, flowing the heavy stripper column bottom stream to a splitter column, producing a light splitter column top stream and a heavy splitter column bottom stream, and recycling at least a portion of the heavy splitter column bottom stream for mixing with the hydrogen feed stream and the hydrocarbon feed stream in the mixing step.

Still some other embodiments of the method include the step of flashing excess hydrogen gas from the hydrogen-enriched liquid hydrocarbon stream before the step of passing. In some embodiments, a molar ratio of hydrogen from the hydrogen feed stream to hydrocarbons in the hydrocarbon feed stream is between about 0.1:1 to about 0.9:1. Still in other embodiments, a molar ratio of hydrogen from the hydrogen feed stream to hydrocarbons in the hydrocarbon feed is between about 0.3:1 to about 0.7:1. Still in other embodiments, the weight percent of mono-aromatics in the product stream increases by between about 0.5% to about 25% compared to the weight percent of mono-aromatics in the hydrocarbon feed stream and the weight percent of di-aromatics in the product stream decreases by between about 5% to about 75% compared to the weight percent of di-aromatics in the hydrocarbon feed stream.

Additionally disclosed is a system for hydrodearylation of non-condensed alkyl-bridged multi-aromatic hydrocarbons, the system including a hydrodearylation reaction zone, the hydrodearylation reaction zone comprising: a hydrocarbon feed stream, a hydrogen feed stream, a mixer operable to mix hydrocarbons from the hydrocarbon feed stream and hydrogen from the hydrogen feed stream to create a hydrogen-enriched liquid hydrocarbon stream, and a hydrodearylation reactor with a catalyst, the hydrodearylation reactor configured to accept an inlet stream comprising only the hydrogen-enriched liquid hydrocarbon stream without a separate gaseous phase of hydrogen gas and configured to produce a product stream, the product stream comprising a reduced concentration of di-aromatic compounds and an increased concentration of mono-aromatic compounds compared to the hydrocarbon feed stream; a separation zone fluidly coupled with the hydrodearylation reaction zone and comprising: a hot separator to separate the product stream into a hydrodearylated gas tops stream and a hydrodearylated liquid bottoms stream, where a portion of the hydrodearylated liquid bottoms stream is recycled for mixing with the hydrogen feed stream and the hydrocarbon feed stream; and a fractionation zone, the fractionation zone fluidly coupled to the separation zone and comprising: a stripper column to produce a light vapor stripper top stream and a heavy stripper column bottom stream, and a splitter column, the splitter column fluidly coupled to the stripper column, and configured to produce a light splitter column top stream and a heavy splitter column bottom stream, and to recycle at least a portion of the heavy splitter column bottom stream for mixing with the hydrogen feed stream and the hydrocarbon feed stream.

In some embodiments of the system, the hydrodearylation reaction zone is operable to process $C_{9+}$ compounds obtained from a xylene rerun column to produce the product stream. In other embodiments, the hydrodearylation reaction zone is operable to process $C_{11+}$ compounds obtained from a xylene rerun column to produce the product stream. Still in other embodiments of the system, the hydrogen feed stream includes a recycled hydrogen stream and a makeup hydrogen stream. In yet other embodiments, the catalyst is presented as a catalyst bed in the hydrodearylation reactor. Still in other embodiments, the catalyst bed includes two or more catalyst beds. Still in other embodiments, the catalyst includes a support being at least one member of the group consisting of silica, alumina, and combinations thereof, and further includes an acidic component being at least one member of the group consisting of amorphous silica-alumina, zeolite, and combinations thereof.

In certain other embodiments of the system, the catalyst includes an IUPAC Group 8-10 metal being at least one member of the group consisting of iron, cobalt, and nickel, and combinations thereof and further includes an IUPAC Group 6 metal being at least one member of the group consisting of molybdenum and tungsten, and combinations thereof. In certain embodiments, the IUPAC Group 8-10 metal is 2 to 20 percent by weight of the catalyst and the IUPAC Group 6 metal is 1 to 25 percent by weight of the catalyst. Still in other embodiments, the catalyst includes at least one of nickel, molybdenum, ultrastable Y-type zeolite, and γ-alumina support. In certain embodiments, the catalyst includes a noble IUPAC Group 8-10 metal. Still in other embodiments, the mixer comprises a first static mixer and a second static mixer, and the first static mixer is operable to mix hydrogen from the hydrogen feed stream, the hydrocarbon feed stream, and the portion of the heavy splitter column bottom stream for mixing with the hydrogen feed stream and the hydrocarbon feed, and where the second static mixer is operable to mix hydrogen from the hydrogen feed stream, the hydrocarbon feed stream, and the portion of the hydrodearylated liquid bottoms stream that is recycled for mixing with the hydrogen feed stream and the hydrocarbon feed stream.

In certain embodiments, the hydrogen feed stream includes a first hydrogen feed stream for hydrogen supply to the first static mixer and a second hydrogen feed stream for hydrogen supply to the second static mixer. Still in other embodiments, the system includes a flashing device in the hydrodearylation reaction zone, preceding the hydrodearylation reactor and fluidly coupled to the hydrodearylation reactor, the flashing device operable to flash any excess hydrogen gas present in the hydrogen-enriched liquid hydrocarbon stream.

BRIEF DESCRIPTION OF THE DRAWING

Embodiments will be readily understood by the following detailed description in conjunction with the accompanying drawing. Embodiments are illustrated by way of example and not by way of limitation in the figures of the accompanying drawing.

DETAILED DESCRIPTION

Figure 1:
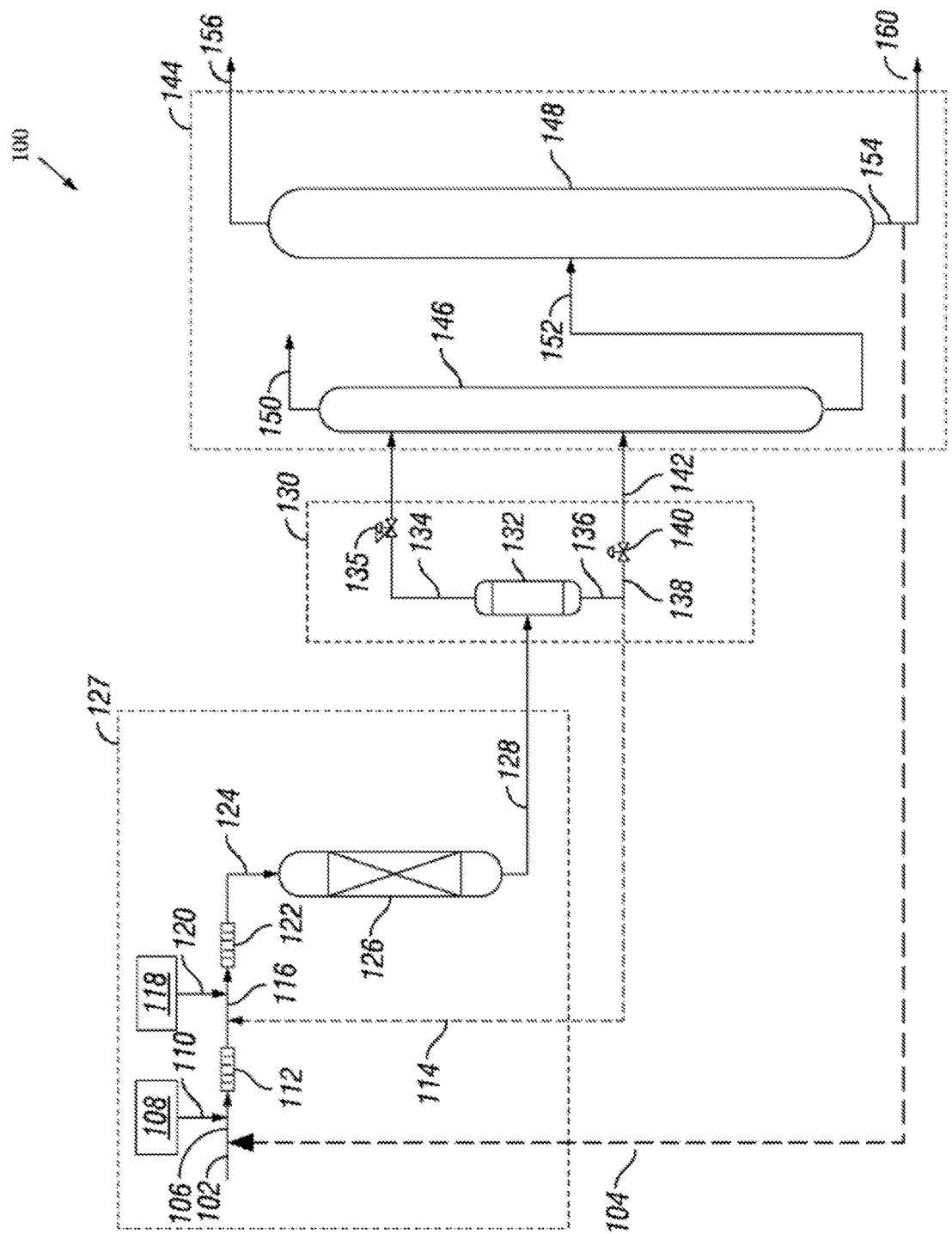
FIG. 1 schematically illustrates a system and process for the conversion of alkyl-bridged non-condensed multi-aromatic compounds to non-condensed alkyl aromatic compounds, in accordance with various embodiments.

The present disclosure describes various embodiments related to processes, devices, and systems for conversion of alkyl-bridged non-condensed multi-aromatic compounds to alkyl mono-aromatic compounds. Further embodiments are described and disclosed.

In the following description, numerous details are set forth in order to provide a thorough understanding of the various embodiments. In other instances, well-known processes, devices, and systems may not been described in particular detail in order not to unnecessarily obscure the various embodiments. Additionally, illustrations of the various embodiments may omit certain features or details in order to not obscure the various embodiments.

In the following detailed description, reference is made to the accompanying drawing that forms a part of this disclosure. The drawing may provide an illustration of some of the various embodiments in which the subject matter of the present disclosure may be practiced. Other embodiments may be utilized, and logical changes may be made without departing from the scope of this disclosure. Therefore, the following detailed description is not to be taken in a limiting sense.

The description may use the phrases "in some embodiments," "in various embodiments," "in an embodiment," or "in embodiments," which may each refer to one or more of the same or different embodiments. Furthermore, the terms "comprising," "including," "having," and the like, as used with respect to embodiments of the present disclosure, are synonymous.

As used in this disclosure, the term "hydrodearylation" refers to a process for the cleaving of the alkyl bridge of non-condensed alkyl-bridged multi-aromatics or heavy alkyl aromatic compounds to form alkyl mono-aromatics or mono-aromatics, in the presence a catalyst and hydrogen.

As used in this disclosure, the term "stream" (and variations of this term, such as hydrocarbon stream, feed stream, product stream, line, and the like) may include one or more of various hydrocarbon compounds, such as straight chain, branched or cyclical alkanes, alkenes, alkadienes, alkynes, alkyl aromatics, alkenyl aromatics, condensed and non-condensed di-, tri- and tetra-aromatics, and gases such as hydrogen and methane, $C_{2+}$ hydrocarbons and further may include various impurities.

As used in this disclosure, the term "zone" refers to an area including one or more equipment, or one or more sub-zones. Equipment may include one or more reactors or reactor vessels, heaters, heat exchangers, pipes, pumps, compressors, and controllers. Additionally, an equipment, such as reactor, dryer, or vessels, further may include one or more zones.

As used in this disclosure, the term "rich" means an amount of at least 50% or greater, by mole percentage of a compound or class of compounds in a stream. Certain streams rich in a compound or class of compounds can contain about 70% or greater, by mole percentage of the particular compound or class of compounds in the streams. In certain cases, mole percentage may be replaced by weight percentage, in accordance with standard industry usage.

As used in this disclosure, the term "substantially" means an amount of at least 80%, by mole percentage of a compound or class of compounds in a stream. Certain streams substantially containing a compound or class of compounds can contain at least 90%, by mole percentage of the compound or class of compounds in the streams. Certain streams substantially containing a compound or class of compounds can contain at least 99%, by mole percentage of the compound or class of compounds in the streams. In certain cases, mole percentage may be replaced by weight percentage, in accordance with standard industry usage.

As used in this disclosure, the term "mixed xylenes" refers to a mixture containing one or more $C_8$ aromatics, including any one of the three isomers of di-methylbenzene and ethylbenzene.

Certain embodiments disclosed here relate to recovery of light alkylated mono-aromatics from streams containing alkyl-bridged non-condensed alkylated multi-aromatic compounds and heavy alkyl-aromatic compounds during a hydrocarbon refining process. Alkyl-bridged non-condensed alkyl aromatic compounds may be referred to as multi-aromatics or poly-aromatics. Conversion of multi-aromatics into alkyl mono-aromatics may be desirable to optimize the use of hydrocarbon process streams containing multi-aromatics. In various embodiments, recovery processes provide alkyl mono-aromatic compounds that have retained the high octane properties of the multi-aromatics.

Retaining a high octane number may be desirable for gasoline blending of the alkyl aromatics. In various embodiments, the density, color, and boiling point properties may be improved by the recovery processes, resulting in a higher value hydrocarbon stream for blending into gasoline streams. In various embodiments, the processes for conversion of multi-aromatics into mono-aromatics, such as alkyl aromatics, may allow for the use of the alkyl aromatics as feedstock to a benzene, toluene, ethylbenzene, and xylenes (BTEX) petrochemicals processing unit. In various embodiments, the processes for conversion of multi-aromatics into alkyl aromatics may allow for the use of the alkyl aromatics as feedstock within a TA/TDP unit. Accordingly, certain embodiments may provide higher value use of a hydrocarbon stream containing multi-aromatics by converting these compounds to alkyl aromatics.

Certain embodiments disclosed here relate to methods for recovery of light alkylated mono-aromatics from streams containing alkyl-bridged non-condensed alkylated multi-aromatic compounds and heavy alkyl-aromatic compounds. The alkyl-bridged non-condensed alkyl aromatic compounds include at least two benzene rings connected by an alkyl bridge group having at least two carbons, wherein the benzene rings are connected to at least two different carbons of the alkyl bridge group. The feed stream can be a $C_{9+}$, $C_{10+}$, or $C_{11+}$ heavy aromatics stream from a xylenes rerun column. The feed stream can be a $C_{9+}$ aromatics stream, which includes di, tri, and poly aromatics ($C_9$ to $C_{16+}$). In certain embodiments, the feed stream may be diluted by a solvent or may be supplied without any dilution by a solvent. In certain embodiments, the feed stream is combined with the hydrogen stream and supplied as a combined stream to the reactor. In certain embodiments, the hydrogen stream includes a combination of a recycled hydrogen stream and a makeup hydrogen stream. The hydrogen stream can contain at least 70% hydrogen by weight.

The catalyst may be provided as a catalyst bed in the reactor. In certain embodiments, a portion of the hydrogen stream is fed to the catalyst bed of the reactor to quench the catalyst bed. The catalyst bed may include two or more catalyst beds. In certain embodiments, the catalyst includes a support selected from the group consisting of silica and alumina, and combinations thereof, and further includes an acidic component selected from the group consisting of amorphous silica-alumina and zeolite, and combinations thereof. The catalyst can include an IUPAC Group 8-10 metal and an IUPAC Group 6 metal. The catalyst can include an IUPAC Group 8-10 metal selected from the group consisting of iron, cobalt, and nickel, and combinations thereof, and further includes an IUPAC Group 6 metal selected from the group consisting of molybdenum and tungsten, and combinations thereof. Certain catalysts used here contain the IUPAC Group 8-10 metal as 2 to 20 percent by weight of the catalyst and the IUPAC Group 6 metal as 1 to 25 percent by weight of the catalyst. The catalyst can include one or more of nickel, molybdenum, ultrastable Y-type zeolite, and γ-alumina support. The reactor is operated under suitable temperature and pressure conditions for optimal recovery of the alkylated mono-aromatics. Such operating conditions can include maintaining the temperature of the reactor between about 200° C. to about 450° C. during the hydrodearylation reaction. Such operating conditions can include maintaining the temperature of the reactor at about 300° C. to about 350° C. during the hydrodearylation reaction.

Certain embodiments of the method can also include the step of supplying, to the reactor, a recycled hydrocarbon stream including a plurality of unreacted alkyl bridged non-condensed alkyl aromatic compounds. In certain embodiments, the recycled hydrocarbon stream is combined with the feed stream and supplied to the reactor as a single stream. In certain embodiments, the hydrogen stream can be combined with the combined feed stream of the recycled hydrocarbon stream and the feed stream and supplied to the reactor as a single stream. Certain embodiments can include supplying the product stream to a separation zone to separate the product into a lighter hydrocarbon stream and a heavier hydrocarbon stream. In certain embodiments, the product stream includes a majority or substantially $C_8$ to $C_{10}$ range alkyl mono-aromatics.

In embodiments disclosed here, hydrogen gas required for hydrodearylation reactions is dissolved in the liquid feedstock prior to the hydrodearylation reactor through one or more mixing device. The mixing device can be a static mixer, or any other kind of mixing apparatus such as a mixing valve.

Referring now to FIG. 1, a schematic illustration is shown for a system and process for the conversion of alkyl-bridged non-condensed multi-aromatic compounds to mono-aromatic compounds, such as light alkyl aromatic compounds, in accordance with various embodiments. The various process flow lines illustrated in FIG. 1 may be referred to as streams, feeds, products, lines, inlets, or effluents. Additionally, not all heat transfer, mass transfer, and fluid conveying equipment are illustrated, and the requirements for these items are well understood by a person of ordinary skill in the art. In hydrodearylation system 100, a feedstock stream 102 mixes with optional recycle stream 104 forming a precursor feed stream 106. Precursor feed stream 106 is mixed with hydrogen gas from make-up hydrogen header 108, proceeding via line 110, in mixer 112. Mixer 112 can be a static mixer, but in other embodiments could be any other mixing device, such as a mixing valve, or combination of suitable mixing devices for mixing heavy non-condensed alkyl-bridged multi-aromatics and hydrogen gas. Mixer 112 contributes to saturating the liquid hydrocarbons with hydrogen gas, without introducing a separate hydrogen gas phase.

Effluent from mixer 112 then further mixes with optional recycle stream 114. Mixed stream 116 is then further mixed with hydrogen gas from make-up hydrogen header 118, proceeding via line 120, in mixer 122 to further saturate the combined feed liquid with hydrogen gas for an amount required for a suitable hydrodearylation reaction with conversion of di-aromatics to mono-aromatics (discussed further with regard to the Examples). Combined effluent stream 124 is then fed to a hydrodearylation reactor 126 in hydrodearylation reactor zone 127. The amount of hydrogen added to the liquid stream is determined by the saturation limits of the fluid at known pressure and temperature. If an amount of hydrogen required for a required conversion reaction is more than the feedstock can absorb, then the product stream is recycled back to the system to provide more medium for hydrogen to dissolve. Combined effluent stream 124 enters hydrodearylation reactor 126 at temperature and pressure conditions near those of the reactor as a hydrogen-saturated liquid. In mixers 112, 122 heating can be applied to heat a feed to proximate the temperature of hydrodearylation reactor 126, for example about 350° C.

Hydrodearylation reactor 126 includes an effective quantity of a suitable catalyst. The catalyst can be disposed in one or more catalyst beds. Hydrodearylation reactor 126 includes an inlet for receiving combined effluent stream 124 containing dissolved hydrogen. Feedstock stream 102 can include $C_{9+}$ aromatics, including $C_{10+}$ and $C_{11+}$ aromatics. Feedstock stream 102 can include only $C_{10+}$ aromatics or only $C_{11+}$ aromatics. Hydrodearylation reactor 126 is a two phase reactor, with liquid feedstock and a solid, heterogeneous catalyst. Light gases (for example, $C_1$-$C_4$) are formed in the reaction and they are released to the vapor phase in the reactor. But at reactor conditions, hydrogen remains in the liquid phase. A hydrodearylated effluent stream 128 is discharged from an outlet of hydrodearylation reactor 126. Hydrodearylation reactor 126 may have a single or multiple catalyst beds. In some embodiments (not pictured) combined effluent stream 124 can enter a flashing device prior to entering hydrodearylation reactor 126 to flash and remove any excess hydrogen in the gas phase.

In various embodiments, the degree of conversion in hydrodearylation reactor zone 127 can be kept below a threshold to limit the amount of catalyst required and the amount of coking on the catalyst. By way of example and not limitation, a threshold limit may be 70% of a maximum potential conversion in hydrodearylation reactor 126. Hydrodearylated effluent stream 128 passes to a separation zone 130. Separation zone 130 includes a hot separator 132. Hot separator 132 includes an inlet for receiving hydrodearylated effluent stream 128, an outlet for discharging a hydrodearylated gas stream 134, and an outlet for discharging a hydrodearylated liquid stream 136. Hot separator 132 is pressure controlled at hydrodearylated gas stream 134 via valve 135. The pressure is controlled such that the reaction zone pressure ensures that the reaction streams are in liquid phase in hydrodearylation reactor 126.

In the embodiment of FIG. 1, hot separator 132 operates at a temperature between about 200° C. and about 240° C. and a pressure less than about 6 bars, which is representative of the pressure drop in the system. The operating conditions of stripper column 146 depend, in part, on the cut point of the products to be separated. The cut point for gasoline is about 180° C., so column 146 is operated to achieve the cut points required at a pressure between about 1 bar to about 3 bar. The same conditions generally apply for splitter column 148. For a given stripper column, gas, steam, or a combination thereof can be applied to the column (streams not pictured in FIG. 1). In gas stripping, for example, nitrogen is a common gas applied as a stripping gas. A stripper column can remove light gases dissolve in a liquid phase.

Hydrodearylated gas stream 134 is a mixture of unreacted hydrogen gas and light gases (for example, $C_1$-$C_4$) from hydrodearylation reactor 126. Hydrodearylated liquid stream 136 splits into two streams, 114 and 138. Recycle stream 114 (a short recycle stream) is recycled back to mix with the effluent stream from mixer 112. Recycle stream 114 acts as both a heat sink and provides necessary liquid feed to dissolve the hydrogen required, in some embodiments. Hydrodearylation reactions, because of hydrogen addition, are exothermic reactions so heat is generated in the process, for example in hydrodearylation reactor 126. Recycle stream 114 can act as a coolant for the system to lower the temperature of the process. Hydrodearylated liquid stream 138 proceeds through level controller and pressure let down valve 140 and forms stream 142, which flows to a fractionation zone 144.

Fractionation zone 144 includes a stripper column 146 and a splitter column 148. The columns 146, 148 can be reboiler fractionation columns, in some embodiments. Stream 142 enters stripper column 146. Stripper column 146 can be a trayed column or a packed column, or a combination of the two types of columns. Stripper column 146 forms two streams, a light vapor stream 150 and a bottom stream 152. Light vapor stream 150 can be condensed, and a portion may be a liquid reflux for stripper column 146. A portion of the condensed and non-condensed vapor of light vapor stream 150 can be routed for further processing. By way of example and not limitation, the condensed and non-condensed vapor in light vapor stream 150 can be processed in a reformate splitter column or a heavy aromatics column within a para-xylene aromatic complex. These details of further processing are not shown in FIG. 1 as they are understood by a person of ordinary skill in the art.

Bottom stream 152 from stripper column 146 is routed into the splitter column 148. Splitter column 148 can be a trayed column or a packed column, or a combination of the two types of columns. Splitter column 148 forms two streams, heavy stream 154 and a light stream 156. The light stream 156 can include $C_{6+}$ compounds. The heavy stream 154 can include $C_{10+}$ compounds, optionally for recycle.

Light stream 156 can be condensed and a portion of the condensed light stream can be liquid refluxed to splitter column 148. A portion of light stream 156 that is not refluxed to splitter column 148 can be routed for further processing. By way of example, some or all of light stream 156 can be routed to a reforming/para-xylene complex for xylene recovery. Heavy stream 154 is split into two streams, a recycle stream 104 (long recycle stream) and a bleed stream 160. A flow rate of bleed stream 160 can be adjusted accordingly to ensure no heavy aromatic hydrocarbon build up in combined effluent stream 124 entering hydrodearylation reactor 126.

In various embodiments, hydrodearylation reactor zone 127 may include two reactors in parallel and may be used with an in-situ regeneration loop. As a fixed bed catalyst system is susceptible to coking when processing heavy aromatics, one reactor may be operating while the other reactor is in a regeneration mode for various embodiments.

In various embodiments, feedstock stream 102 can be a heavy hydrocarbons stream. The heavy hydrocarbons stream can include $C_{9+}$ or $C_{10+}$ or $C_{11+}$ compounds from a xylene rerun column or a heavy aromatic column bottoms from a para-xylene aromatic complex. Feedstock stream 102 can include $C_9$ to $C_{16+}$, and this stream can be predominantly mono-aromatics, di-aromatics, and poly-aromatics.

In various embodiments, hydrodearylation reactor zone 127 can include a reactor having a single catalyst bed or multiple catalyst beds.

EXAMPLES

A simulation was conducted using PRO/II Process Engineering software by AVEVA' to quantify hydrogen gas dissolved in a hydrocarbon feedstock including xylene rerun column bottoms, the properties and compositions of which are shown in Table 1. The feedstock had a color of 20 on the standard reference method scale and a density of 912.5 kg/m$^3$.

TABLE 1

Properties and composition of hydrocarbon feedstock including xylene rerun column bottoms.

| Property/Composition | Unit | Value |
|---|---|---|
| Density | Kg/Lt | 0.9125 |
| Sulfur | ppmw | <5 |
| Nitrogen | ppmw | <5 |
| Compound Type Distribution | | |
| Paraffins | W % | 1.00 |
| Mono Aromatics | W % | 74.60 |
| Naphtheno Mono Aromatics | W % | 3.06 |
| Diaromatics + condensed diaromatics | W % | 15.36 |
| Naphtheno Di Aromatics | W % | 5.21 |
| Tri Aromatics | W % | 0.59 |
| Tetra Aromatics | W % | 0.18 |
| Distillation (ASTM D2298) | | |
| IBP | ° C. | 182 |
| 5 W % | ° C. | 183 |
| 10 W % | ° C. | 183 |
| 30 W % | ° C. | 184 |
| 50 W % | ° C. | 208 |
| 70 W % | ° C. | 302 |
| 90 W % | ° C. | 330 |
| 95 W % | ° C. | 337 |
| FBP | ° C. | 350 |

Simulation conditions at 40 barg pressure and a temperature range of 200° C. to 400° C. are illustrated in Table 2. As shown, the feedstock was all in liquid phase, and there was sufficient hydrogen dissolved in the liquid phase for effecting hydrodearylation reactions. A suitable hydrogen to feed mole ratio is calculated from the data (last column in Table 2). For example, in the embodiment shown, about 0.5 mole of hydrogen is available per one mole hydrocarbon feedstock for effecting hydrodearylation reactions.

TABLE 2

Simulation conditions for hydrodearylation of hydrocarbon feedstock including xylene rerun column bottoms.

| Pressure bars | Temp. ° C. | Vapor Phase W % | Liquid Phase Feedstock W % | Liquid Phase H$_2$ W % | H$_2$ to Feed Mol Ratio |
|---|---|---|---|---|---|
| 40 | 200 | 0.00 | 99.99 | 0.7373 | 0.608141 |
| 40 | 250 | 0.00 | 99.99 | 0.7373 | 0.608141 |
| 40 | 300 | 0.00 | 99.99 | 0.7373 | 0.608141 |
| 40 | 310 | 0.00 | 99.99 | 0.7373 | 0.608141 |
| 40 | 320 | 0.00 | 99.99 | 0.7373 | 0.608141 |
| 40 | 330 | 0.00 | 99.99 | 0.7373 | 0.608141 |
| 40 | 340 | 0.00 | 99.99 | 0.7373 | 0.608141 |

TABLE 2-continued

Simulation conditions for hydrodearylation of hydrocarbon feedstock including xylene rerun column bottoms.

| Pressure bars | Temp. °C. | Vapor Phase W % | Liquid Phase Feedstock W % | Liquid Phase $H_2$ W % | $H_2$ to Feed Mol Ratio |
|---|---|---|---|---|---|
| 40 | 350 | 0.00 | 99.99 | 0.7373 | 0.608141 |
| 40 | 360 | 0.00 | 99.99 | 0.7373 | 0.608141 |
| 40 | 370 | 0.00 | 99.99 | 0.7242 | 0.597685 |
| 40 | 380 | 0.00 | 99.99 | 0.7242 | 0.598883 |
| 40 | 400 | 0.00 | 99.99 | 0.6048 | 0.505459 |
| 40 | 410 | 0.00 | 99.99 | 0.6048 | 0.505459 |

After hydrogen is dissolved in the feedstock, the liquid phase feedstock containing liquid phase hydrogen is reacted in a hydrodearylation reaction zone over a catalyst containing a Y zeolite as a support with an alumina binder and nickel and molybdenum as active phase components and operated at hydrodearylation conditions at a temperature range of 200° C. to 450° C., a pressure of 15 barg, a liquid hourly space velocity in the range of 1.2-1.3 $hr^{-1}$, and at a hydrogen to hydrocarbon nominal minimum mole ratio of 0.5. The reaction operating conditions, product yield, product composition, and conversion data are summarized in Table 3.

TABLE 3

Simulation conditions and results for hydrodearylation of hydrocarbon feedstock including xylene rerun column bottoms.

| Condition | | Feedstock | 1 | 2 | 3 | 4 | 5 |
|---|---|---|---|---|---|---|---|
| Pressure | barg | | 15 | 15 | 15 | 15 | 15 |
| Weighted Average Bed Temperature (WABT) | °C. | | 201 | 251 | 299 | 349 | 400 |
| Liquid Hourly Space Velicity (LHSV) | $h^{-1}$ | | 1.198 | 1.173 | 1.253 | 1.255 | 1.306 |
| Yields | | | | | | | |
| Total Liquid Product | W % | | 99.91 | 99.91 | 99.91 | 99.92 | 99.53 |
| Gas | W % | | 0.09 | 0.09 | 0.09 | 0.08 | 0.47 |
| Total | W % | | 100.00 | 100.00 | 100.00 | 100.00 | 100.00 |
| Property | | | | | | | |
| API Gravity | ° | 23.6 | 26.8 | 26.8 | 27.8 | 29.2 | 29.2 |
| Product Composition | | | | | | | |
| Paraffins and Naphthenes | W % | 1.0 | 1.8 | 1.6 | 1.3 | 1.3 | 1.3 |
| Mono-aromatics | W % | 74.6 | 75.0 | 75.1 | 81.8 | 90.2 | 90.2 |
| Di-aromatics | W % | 15.4 | 14.2 | 14.0 | 8.4 | 3.8 | 4.2 |
| Tri-aromatics and Tetra-aromatics | W % | 0.8 | 0.6 | 0.6 | 0.5 | 0.6 | 0.6 |
| Di-aromatics Conversion | W % | | 7.5 | 8.9 | 45.6 | 75.3 | 73.0 |

As seen from the compositions of the products, aromatics with two rings are converted to mono-aromatics. The conversion of di-aromatics compounds is about 8% at 200-250° C. and increases with increasing temperature. At 300° C. the conversion increases to about 46% while further increasing the temperature to 350-400° C. results in a conversion rate of about 74%. The density changes also confirm the transformation: a 5.6 degrees API gravity improvement is observed.

A sample of xylene rerun column bottoms was tested in a pilot plant. A commercial hydrocracking catalyst, previously used for hydrotreating tests, was loaded into the pilot plant reactor, and the pilot plant was operated first at 15 barg pressure at temperatures from about 200° C. to about 450° C., and then at 25 barg pressure at temperatures from about 300° C. to 400° C. Hydrodearylation was observed with only hydrogen dissolved in the xylene rerun column bottoms.

Therefore, provided here are processes and systems for dearylation of $C_{9+}$ compounds, for example $C_9$-$C_{16}$ compounds, from aromatic complex bottoms into gasoline blending components or chemicals including benzene, xylenes, and toluene in a catalytic hydrodearylation reactor. The processes and systems can include mixing a liquid hydrocarbon feedstock with an excess of hydrogen gas in a mixing zone to dissolve a portion of the hydrogen gas in the liquid hydrocarbon feedstock to produce a hydrogen-enriched liquid hydrocarbon feedstock; conveying the hydrogen-enriched liquid hydrocarbon feedstock and any undissolved hydrogen to an optional flashing zone in which at least a portion or substantially all of the undissolved hydrogen is flashed, passing the hydrogen-enriched liquid hydrocarbon feedstock from the flashing zone to a feed inlet of a dearylation reactor; recovering, from the reactor, a product stream for a downstream process, wherein the alkyl-bridged non-condensed alkyl multi-aromatic compounds fed into the hydrodearylation reactor include at least two benzene rings connected by an alkyl bridge group having at least two carbons, wherein the benzene rings are connected to different carbons of the alkyl bridge group.

Embodiments of the disclosure can be applied to increase yields of benzene and para-xylene in aromatics complexes for the production of aromatics. Aromatics and gasoline volume yields can be increased, and improvements to color and boiling point properties of a gasoline blend stream are realized.

In some refineries and plants, the bottoms stream from a heavy aromatics column is used as fuel oil to be burned in heaters. A significant portion of this low-value stream can be recovered using embodiments of the disclosure, resulting in increased yields of benzene and para-xylene. In some refineries and plants, where the bottoms stream of a xylenes rerun column is sent for gasoline blending, the dark brown color, the high boiling points, and the high density of the stream are outside the desired gasoline specification, requiring dilution with other streams to meet the overall specification. By applying embodiments disclosed here, the color is greatly improved, the boiling point of much of the stream is reduced, and the density is greatly decreased. The density decrease results in volume swell, increasing the overall volume of produced gasoline.

In various embodiments, the alkyl bridged non-condensed multi-aromatic compounds include at least two benzene rings connected by an alkyl bridge group having at least two carbons, where the benzene rings are connected to different carbons of the alkyl bridge group. In various embodiments, the alkyl bridged non-condensed multi-aromatic compounds include additional alkyl groups connected to the benzene rings of the alkyl bridged non-condensed multi-aromatic compounds. The hydrocarbon feedstock can be a stream in a petroleum refinery from one or more hydrocarbons treatments. In various embodiments, the hydrocarbon feedstock may comprise a heavy aromatics stream from a unit operation of a petroleum refinery. In various embodiments, the hydrocarbon feedstock may comprise a $C_{9+}$, $C_{10+}$, or $C_{11+}$ heavy aromatics stream from a xylene rerun column of a petroleum refinery. In various embodiments, the hydrocarbon feedstock is undiluted by a solvent.

By way of example and not limitation, the various alkyl bridged non-condensed multi-aromatic compounds may include a mixture of chemical compounds illustrated by Formula I, Formula II, and Formula III, and various combinations of these compounds.

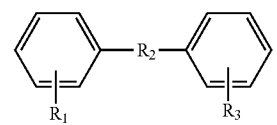

[Formula I]

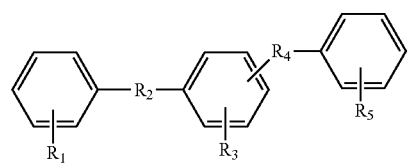

[Formula II]

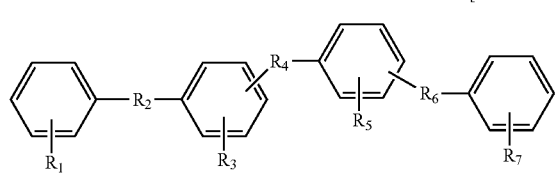

[Formula III]

$R_2$, $R_4$, and $R_6$ are alkyl bridge groups independently having from two to six carbon atoms. $R_1$, $R_3$, $R_5$, and $R_7$ are independently selected from the group consisting of hydrogen and an alkyl group having from one to eight carbon atoms. In addition to the groups $R_1$, $R_3$, $R_5$, and $R_7$, the benzene groups of Formulas I, II, and III may further include additional alkyl groups connected to the benzene groups, respectively. In addition to the four benzene groups of Formula III, the various alkyl bridged non-condensed alkyl aromatic compounds may include five or more benzene groups connected by alkyl bridges, where the additional benzene groups further may include alkyl groups connected to the additional benzene groups.

In various embodiments, a hydrogen supply stream from a hydrogen header may contain at least 70 mole percent hydrogen. In various embodiments, the hydrogen stream may contain at least 80 mole percent hydrogen. In various embodiments, the hydrogen stream may contain at least 90 mole percent hydrogen.

In some embodiments, allowing a hydrodearylation reaction to occur in the presence of a catalyst under suitable reaction conditions causes the alkyl bridges of the alkyl bridged non-condensed multi-aromatic compounds and heavy alkyl aromatic compounds to be cleaved to produce light alkyl mono-aromatic compounds. In various embodiments, non-bridging alkyl groups connected to the benzene rings of the alkyl bridged non-condensed alkyl aromatic compounds remain connected to the benzene rings of the non-condensed alkyl aromatic compounds in the hydrocarbon product. By way of example and not limitation, the various alkyl mono-aromatic compounds may include a mixture of chemical compounds illustrated by Formula IV.

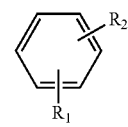

[Formula IV]

For the various alkyl mono-aromatic compounds, $R_1$ is independently selected from the group consisting of hydrogen and an alkyl group having from one to eight carbon atoms, and $R_2$ is independently selected from the group consisting of hydrogen and an alkyl group having from one to eight carbon atoms.

In various embodiments, an operating temperature of a hydrodearylation reactor may be 200 to 450° C., within reasonable engineering tolerances, during the cleaving of the alkyl bridges. In various embodiments, the operating temperature for the reactor may be approximately 300° C., within reasonable engineering tolerances, for the cleaving of the alkyl bridges. In various embodiments, the operating temperature for the reactor may be 350° C., within reasonable engineering tolerances, for the cleaving of the alkyl bridges.

In various embodiments, suitable hydrodearylation reactors can contain a catalyst having at least one IUPAC Group 8-10 metal, and at least one IUPAC Group 6 metal. The IUPAC Group 8-10 metal may be selected from the group consisting of iron, cobalt, and nickel, and combinations thereof. The IUPAC Group 6 metal may be selected from a group consisting of molybdenum and tungsten, and combinations thereof. The IUPAC Group 8-10 metal may be present in an amount of approximately 2-20% by weight, and the IUPAC Group 6 metal may be present in an amount of approximately 1-25% by weight. In various embodiments, the IUPAC Group 8-10 and IUPAC Group 6 metals may be on a support material. In various embodiments, the support material may be silica or alumina, and may further include an acidic component selected from the group consisting of an amorphous silica alumina, a zeolite or a combination of the two. In various embodiments, a hydrodearylation reactor may contain a catalyst having any noble IUPAC Group 8-10 metal on a silica-alumina or alumina support having an acid cracking component of an amorphous silica-alumina or a zeolite, or a combination of the two. In certain embodiments, a hydrodearylation reactor can contain a catalyst selected from the group consisting of platinum, palladium, and combinations thereof, on a silica-alumina or alumina support having an acid cracking component of an amorphous silica-alumina or a zeolite, or a combination of the two.

Figure 2:
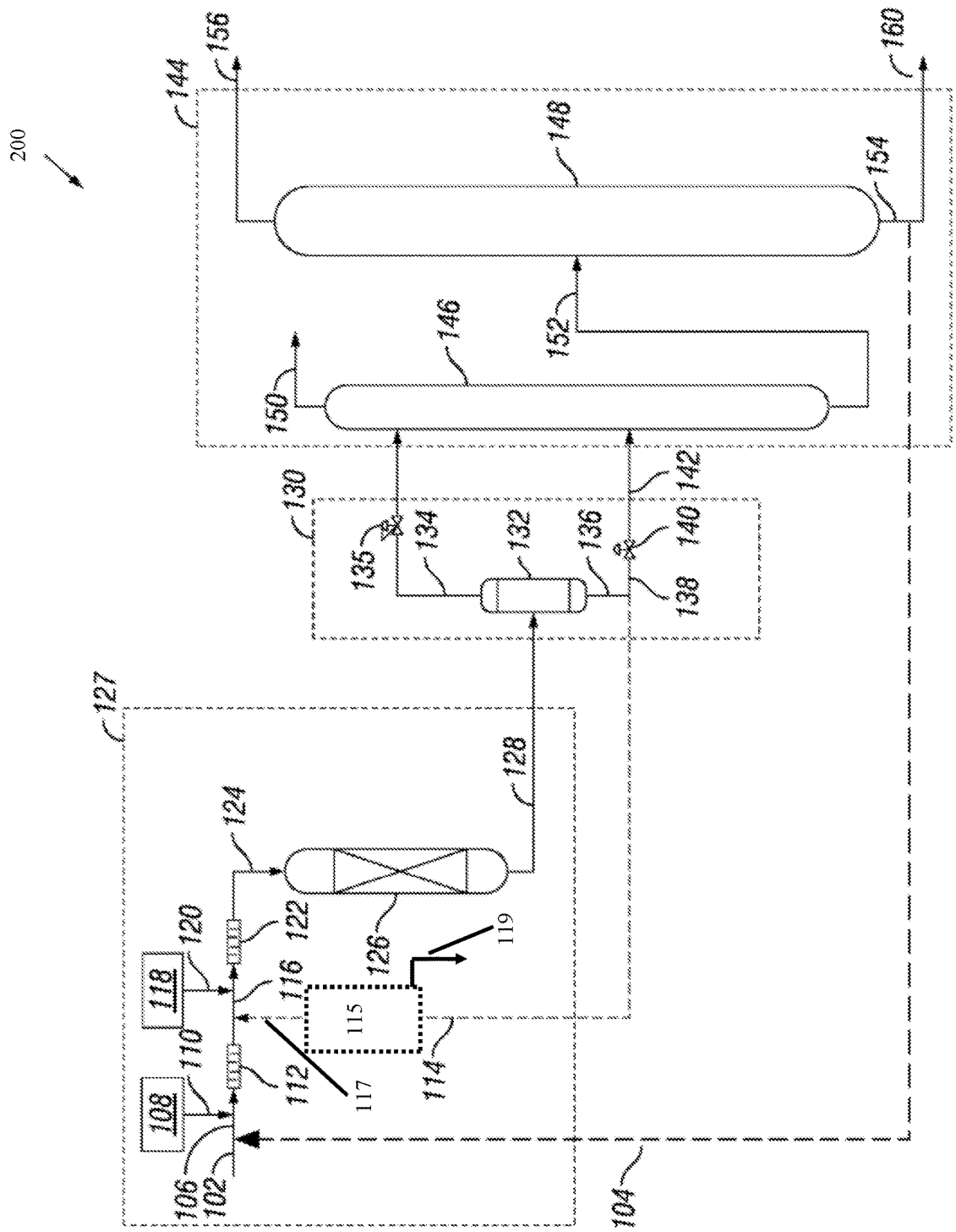
FIG. 2 schematically illustrates a system and process for the conversion of alkyl-bridged non-condensed multi-aromatic compounds to non-condensed alkyl aromatic compounds with fractionation, in accordance with various embodiments.

FIG. 2 schematically illustrates a system and process for the conversion of alkyl-bridged non-condensed multi-aromatic compounds to non-condensed alkyl aromatic compounds with fractionation, in accordance with various embodiments. Units, components, and streams labeled similarly to FIG. 1 are the same or similar to those described for FIG. 1. In hydrodearylation system 200, recycle stream 114 (a short recycle stream) is recycled back for fractionation in optional fractionation unit 115, prior to mixing with the effluent stream from mixer 112 via stream 117. Stream 117 acts as both a heat sink and provides necessary liquid feed to dissolve the hydrogen required, in some embodiments. Hydrodearylation reactions, because of hydrogen addition, are exothermic reactions so heat is generated in the process, for example in hydrodearylation reactor 126. Recycle stream 117 can act as a coolant for the system to lower the temperature of the process. Hydrodearylated liquid stream 138 proceeds through level controller and pressure let down valve 140 and forms stream 142, which flows to a fractionation zone 144.

Recycle stream 114 includes a portion of the hydrodearylated liquid product stream in its entirety, or in other words also includes high-value mono-aromatic compounds, such as BTX. In the embodiment of FIG. 2, with optional fractionation unit 115, consideration can be given not to send the high-value mono-aromatic compounds, produced in hydrodearylation reactor 126, back to the hydrodearylation reactor 126. Recycle stream 114, containing hydrodearylated liquid products including BTX, can be fractionated in order to only send a bottoms product stream 117, containing only compounds with a boiling point of about 180° C. or greater (or $C_{11+}$ compounds or $C_{9+}$ compounds), back to hydrodearylation reactor 126 via streams 117, 116, 124.

A tops stream 119, containing only compounds with a boiling point of about 180° C. or less, can be sent to another part of a refinery for further processing, e.g. transalkylation. In other words, optional fractionation unit 115 is operable to separate the inlet recycle stream 114 into a tops stream or tops fraction 119 (being a stream boiling at or below about 180° C., or a stream containing only $C_9$, $C_{10}$ or lower carbon number compounds) and a bottoms fraction, stream 117 (being a stream of $C_{11+}$ compounds or $C_{9+}$ compounds or boiling at or above about 180° C.). In certain embodiments, optional fractionation unit 115 operates at about atmospheric pressure, with stages or trays operating between about 150-250° C. or about 170-200° C. The wt. % of the high value mono-aromatics or stream boiling at or below about 180° C. can range from about 3-85 wt. % of recycle stream 114.

In embodiments described throughout, inorganic oxides can act as a binder for catalysts, also referred to as a granulating agent. Exemplary inorganic oxides include, but are not limited to, alumina, silica, titania, silica-alumina, alumina-titania, alumina-zirconia, alumina-boria, phosphorus-alumina, silica-alumina-boria, phosphorus-alumina-boria, phosphorus-alumina-silica, silica-alumina-titania, and silica-alumina-zirconia. A catalyst zeolite and the binder can be referred to as the carrier, and in certain embodiments, a zeolite wt. % range in a carrier is between about 1-99 wt. %, or between about 5-70 wt. %. A binder wt. % range in a carrier is between about 1-99 wt. %, or between about 30-95 wt. %. Doping a binder with inorganic oxide materials can induce changes to the properties of a catalyst. For example, phosphorus can act as a stabilizer to a zeolite. Titania can induce changes to the acidity of the catalyst. Inorganic oxides can be used as a catalyst support in certain embodiments where they possess acidity. For example, silica-alumina-titania and silica-titania possess sufficient acidity to be used as catalyst supports. Titania can be used to increase the stability of certain catalysts.

Ranges may be expressed herein as from about one particular value and to about another particular value. When such a range is expressed, it is to be understood that another embodiment is from the one particular value and/or to the other particular value, along with all combinations within said range. Where the range of values is described or referenced herein, the interval encompasses each intervening value between the upper limit and the lower limit as well as the upper limit and the lower limit and includes smaller ranges of the interval subject to any specific exclusion provided. The term "about" when used with respect to a value or range refers to values including plus and minus 5% of the given value or range.

Where a method comprising two or more defined steps is recited or referenced herein, the defined steps can be carried out in any order or simultaneously except where the context excludes that possibility.

While various embodiments have been described in detail for the purpose of illustration, they are not to be construed as limiting, but are intended to cover all the changes and modifications within the spirit and scope thereof.

What is claimed is:

1. A method for hydrodearylation of a hydrocarbon feed stream comprising non-condensed alkyl-bridged multi-aromatic hydrocarbons, the method comprising the steps of:
    supplying a hydrogen feed stream to the hydrocarbon feed stream comprising non-condensed alkyl-bridged multi-aromatic hydrocarbons;
    mixing the hydrogen feed stream with the hydrocarbon feed stream to saturate the hydrocarbon feed stream with hydrogen gas to create a hydrogen-enriched liquid hydrocarbon stream;
    passing the hydrogen-enriched liquid hydrocarbon stream to a hydrodearylation reactor without a separate gaseous phase of hydrogen; and
    allowing the hydrogen-enriched liquid hydrocarbon stream to react in presence of a catalyst under specific reaction conditions as a liquid, in a two phase reactor without a separate hydrogen gas phase outside of hydrogen dissolved in the hydrogen-enriched liquid, to produce a product stream comprising a reduced concentration of di-aromatic compounds and an increased concentration of mono-aromatic compounds compared to the hydrocarbon feed stream comprising non-condensed alkyl-bridged multi-aromatic hydrocarbons;
    where the non-condensed alkyl-bridged multi-aromatic hydrocarbons include at least two benzene rings connected by an alkyl bridge group having at least two carbons, where the benzene rings are connected to different carbons of the alkyl bridge group.

2. The method of claim 1, further comprising the step of recovering, from the hydrodearylation reactor, the product stream for a downstream process.

3. The method of claim 1, where the hydrocarbon feed stream comprises $C_{9+}$ compounds obtained from a xylene rerun column.

4. The method of claim 1, where the hydrocarbon feed stream comprises $C_{11+}$ compounds obtained from a xylene rerun column.

5. The method of claim 1, where the hydrocarbon feed stream comprises hydrocarbon compounds with a boiling point of about 180° C. and greater.

6. The method of claim 1, where the hydrogen feed stream includes a recycled hydrogen stream and a makeup hydrogen stream.

7. The method of claim 1, where the hydrogen feed stream comprises at least 70% hydrogen by weight.

8. The method of claim 1, where the catalyst is presented as a catalyst bed in the hydrodearylation reactor.

9. The method of claim 8, where the catalyst bed includes two or more catalyst beds.

10. The method of claim 1, where the catalyst includes a support being at least one member of the group consisting of silica, alumina, and combinations thereof, and further includes an acidic component being at least one member of the group consisting of amorphous silica-alumina, zeolite, and combinations thereof.

11. The method of claim 10, where the catalyst includes an IUPAC Group 8-10 metal being at least one member of the group consisting of iron, cobalt, and nickel, and combinations thereof and further includes an IUPAC Group 6 metal being at least one member of the group consisting of molybdenum and tungsten, and combinations thereof.

12. The method of claim 11, where the IUPAC 8-10 metal is 2 to 20 percent by weight of the catalyst and the IUPAC Group 6 metal is 1 to 25 percent by weight of the catalyst.

13. The method of claim 1, where the catalyst includes at least one of nickel, molybdenum, ultrastable Y-type zeolite, and γ-alumina support.

14. The method of claim 1, where the catalyst includes a noble IUPAC Group 8-10 metal.

15. The method of claim 1, where the catalyst includes a binder selected from the group consisting of: alumina, silica, titania, silica-alumina, alumina-titania, alumina-zirconia, alumina-boria, phosphorus-alumina, silica-alumina-boria, phosphorus-alumina-boria, phosphorus-alumina-silica, silica-alumina-titania, and silica-alumina-zirconia.

16. The method of claim 1, where specific reaction conditions include an operating temperature of the hydrodearylation reactor being in the range of about 200° C. to about 450° C.

17. The method of claim 16, where the operating temperature of the hydrodearylation reactor is about 300° C.

18. The method of claim 16, where the operating temperature of the reactor is about 350° C.

19. The method of claim 1, where the mixing step comprises a first mixing step and a second mixing step, where the first mixing step mixes a first hydrocarbon recycle stream with the hydrocarbon feed stream, and where the second mixing step mixes a second hydrocarbon recycle stream with the hydrocarbon feed stream.

20. The method of claim 19, where the step of supplying a hydrogen feed stream comprises a first step of supplying a hydrogen feed stream and a second step of supplying a hydrogen feed stream, the first step of supplying a hydrogen feed stream occurring before the first mixing step, and the second step of supplying a hydrogen feed stream occurring before the second mixing step.

21. The method of claim 19, where the first mixing step uses a static mixer to mix hydrogen, the hydrocarbon feed stream, and the first hydrocarbon recycle stream, and where the second mixing step uses a static mixer to mix hydrogen, the hydrocarbon feed stream, and the second hydrocarbon recycle stream.

22. The method of claim 1, further comprising the step of flowing the product stream to a separation zone with a hot separator to separate the product stream into a hydrodearylated gas tops stream and a hydrodearylated liquid bottoms stream, where a portion of the hydrodearylated liquid bottoms stream is recycled for mixing with the hydrogen feed stream and the hydrocarbon feed stream in the mixing step.

23. The method of claim 22, further comprising the steps of flowing the hydrodearylated gas tops stream and a remaining portion of the hydrodearylated liquid bottoms stream to a stripper column of a fractionation zone, producing a light vapor stripper top stream and a heavy stripper column bottom stream, flowing the heavy stripper column bottom stream to a splitter column, producing a light splitter column top stream and a heavy splitter column bottom stream, and recycling at least a portion of the heavy splitter column bottom stream for mixing with the hydrogen feed stream and the hydrocarbon feed stream in the mixing step.

24. The method of claim 1, further comprising the step of flashing excess hydrogen gas from the hydrogen-enriched liquid hydrocarbon stream before the step of passing.

25. The method of claim 1, where a molar ratio of hydrogen from the hydrogen feed stream to hydrocarbons in the hydrocarbon feed stream is between about 0.1:1 to about 0.9:1.

26. The method of claim 1, where a molar ratio of hydrogen from the hydrogen feed stream to hydrocarbons in the hydrocarbon feed is between about 0.3:1 to about 0.7:1.

27. The method of claim 1, where the weight percent of mono-aromatics in the product stream increases by between about 0.5% to about 25% compared to the weight percent of mono-aromatics in the hydrocarbon feed stream and where the weight percent of di-aromatics in the product stream decreases by between about 5% to about 75% compared to the weight percent of di-aromatics in the hydrocarbon feed stream.

28. The method of claim 1, further comprising the step of recycling a first fractionation stream to the mixing step after fractionation of a portion of the product stream into the first fractionation stream comprising hydrocarbon components with a boiling point of greater than about 180° C. and a second fractionation stream comprising mono-aromatic hydrocarbon components with a boiling point of less than about 180° C., where the second fractionation stream proceeds for further processing in a refinery.

29. The method of claim 1, wherein the pressure of the hydrodearylation reactor is between about 5 bar gauge and about 80 bar gauge.

30. A system for hydrodearylation of non-condensed alkyl-bridged multi-aromatic hydrocarbons, the system comprising:
   a hydrodearylation reaction zone, the hydrodearylation reaction zone comprising:
      a hydrocarbon feed stream, a hydrogen feed stream, a mixer operable to mix hydrocarbons from the hydrocarbon feed stream and hydrogen from the hydrogen feed stream to create a hydrogen-enriched liquid hydrocarbon stream, and a 2-phase hydrodearylation reactor with a catalyst, the hydrodearylation reactor configured to accept an inlet stream comprising only the hydrogen-enriched liquid hydrocarbon stream and react without a separate gaseous phase of hydrogen gas and configured to produce a product stream, the product stream comprising a reduced concentration of di-aromatic compounds and an increased concentration of mono-aromatic compounds compared to the hydrocarbon feed stream.

31. The system of claim 30, further comprising:
a separation zone fluidly coupled with the hydrodearylation reaction zone and comprising:
a hot separator to separate the product stream into a hydrodearylated gas tops stream and a hydrodearylated liquid bottoms stream, where a portion of the hydrodearylated liquid bottoms stream is recycled for mixing with the hydrogen feed stream and the hydrocarbon feed stream; and
a fractionation zone, the fractionation zone fluidly coupled to the separation zone and comprising:
a stripper column to produce a light vapor stripper top stream and a heavy stripper column bottom stream, and a splitter column, the splitter column fluidly coupled to the stripper column, and configured to produce a light splitter column top stream and a heavy splitter column bottom stream, and to recycle at least a portion of the heavy splitter column bottom stream for mixing with the hydrogen feed stream and the hydrocarbon feed stream.

32. The system of claim 30, where the hydrodearylation reaction zone is operable to process $C_{9+}$ compounds obtained from a xylene rerun column to produce the product stream.

33. The system of claim 30, where the hydrodearylation reaction zone is operable to process $C_{11+}$ compounds obtained from a xylene rerun column to produce the product stream.

34. The system of claim 30, where the hydrodearylation reaction zone is operable to process a hydrocarbon feed stream comprising hydrocarbon compounds with a boiling point of about 180° C. and greater.

35. The system of claim 30, where the hydrogen feed stream includes a recycled hydrogen stream and a makeup hydrogen stream.

36. The system of claim 30, where the catalyst is presented as a catalyst bed in the hydrodearylation reactor.

37. The system of claim 36, where the catalyst bed includes two or more catalyst beds.

38. The system of claim 30, where the catalyst includes a support being at least one member of the group consisting of silica, alumina, and combinations thereof, and further includes an acidic component being at least one member of the group consisting of amorphous silica-alumina, zeolite, and combinations thereof.

39. The system of claim 38, where the catalyst includes an IUPAC Group 8-10 metal being at least one member of the group consisting of iron, cobalt, and nickel, and combinations thereof and further includes an IUPAC Group 6 metal being at least one member of the group consisting of molybdenum and tungsten, and combinations thereof.

40. The system of claim 39, where the IUPAC 8-10 metal is 2 to 20 percent by weight of the catalyst and the IUPAC Group 6 metal is 1 to 25 percent by weight of the catalyst.

41. The system of claim 30, where the catalyst includes at least one of nickel, molybdenum, ultrastable Y-type zeolite, and γ-alumina support.

42. The system of claim 30, where the catalyst includes a noble IUPAC Group 8-10 metal.

43. The system of claim 30, where the catalyst includes a binder selected from the group consisting of: alumina, silica, titania, silica-alumina, alumina-titania, alumina-zirconia, alumina-boria, phosphorus-alumina, silica-alumina-boria, phosphorus-alumina-boria, phosphorus-alumina-silica, silica-alumina-titania, and silica-alumina-zirconia.

44. The system of claim 31, where the mixer comprises a first static mixer and a second static mixer, and where the first static mixer is operable to mix hydrogen from the hydrogen feed stream, the hydrocarbon feed stream, and the portion of the heavy splitter column bottom stream for mixing with the hydrogen feed stream and the hydrocarbon feed, and where the second static mixer is operable to mix hydrogen from the hydrogen feed stream, the hydrocarbon feed stream, and the portion of the hydrodearylated liquid bottoms stream that is recycled for mixing with the hydrogen feed stream and the hydrocarbon feed stream.

45. The system of claim 44, where the hydrogen feed stream includes a first hydrogen feed stream for hydrogen supply to the first static mixer and a second hydrogen feed stream for hydrogen supply to the second static mixer.

46. The system of claim 30, further comprising a flashing device in the hydrodearylation reaction zone, preceding the hydrodearylation reactor and fluidly coupled to the hydrodearylation reactor, the flashing device operable to flash any excess hydrogen gas present in the hydrogen-enriched liquid hydrocarbon stream.

47. The system of claim 30, further comprising a fractionation unit in fluid communication with the product stream, the fractionation unit operable to produce a first fractionation stream for recycle to the mixer after fractionation, the first fractionation stream comprising hydrocarbon components with a boiling point of greater than about 180° C., and the fractionation unit operable to produce a second fractionation stream comprising mono-aromatic hydrocarbon components with a boiling point of less than about 180° C., where the second fractionation stream proceeds for further processing in a refinery.

48. The system of claim 30, wherein the pressure of the hydrodearylation reactor is between about 5 bar gauge and about 80 bar gauge.

* * * * *